United States Patent
Munday

(10) Patent No.: US 7,621,749 B2
(45) Date of Patent: Nov. 24, 2009

(54) KIT, INJECTABLE OBJECT, AIDS AND A METHOD OF USING THEM FOR PRACTICING HYPODERMIC NEEDLE INSERTION TECHNIQUES

(75) Inventor: Laurie D. Munday, San Diego, CA (US)

(73) Assignee: Wallcur, Inc., San Diego, CA (US)

( * ) Notice: Subject to any disclaimer, the term of this patent is extended or adjusted under 35 U.S.C. 154(b) by 574 days.

(21) Appl. No.: 11/429,097

(22) Filed: May 5, 2006

(65) Prior Publication Data

US 2007/0260182 A1 Nov. 8, 2007

(51) Int. Cl.
G09B 23/28 (2006.01)

(52) U.S. Cl. ..................................... 434/262

(58) Field of Classification Search ............... 434/262, 434/267, 269, 272; 604/116
See application file for complete search history.

(56) References Cited

U.S. PATENT DOCUMENTS

| | | | | |
|---|---|---|---|---|
| 2,689,415 A * | 9/1954 | Haver | .......................... | 434/272 |
| 2,781,611 A * | 2/1957 | Bills et al. | .................. | 446/224 |
| 3,339,290 A * | 9/1967 | Doyle | .......................... | 434/267 |
| 3,542,022 A * | 11/1970 | Bartnik | ........................ | 604/116 |
| 3,704,529 A * | 12/1972 | Cioppa | .......................... | 434/272 |
| 4,198,766 A * | 4/1980 | Camin | .......................... | 434/272 |
| 4,228,796 A * | 10/1980 | Gardiner | ..................... | 604/116 |
| 4,349,338 A * | 9/1982 | Heppler | ...................... | 434/262 |
| 4,362,157 A * | 12/1982 | Keeth | .......................... | 604/116 |
| 5,314,339 A * | 5/1994 | Aponte | ........................ | 434/267 |
| 5,634,904 A * | 6/1997 | Battenfield | ................... | 604/116 |
| 5,839,904 A * | 11/1998 | Bloom | ......................... | 434/268 |
| 5,842,870 A * | 12/1998 | Cramer | ........................ | 434/267 |
| 6,004,136 A * | 12/1999 | Ehrenpreis | .................. | 434/262 |
| 6,234,804 B1 * | 5/2001 | Yong | ............................ | 434/267 |
| 6,336,812 B1 * | 1/2002 | Cooper et al. | ............... | 434/267 |
| 2006/0105309 A1 * | 5/2006 | Stoll et al. | .................. | 434/262 |
| 2006/0204939 A1 * | 9/2006 | Bardsley et al. | ............. | 434/262 |

* cited by examiner

*Primary Examiner*—Kurt Fernstrom
(74) *Attorney, Agent, or Firm*—Bernard L. Kleinke; Duckor Spradling Metzger & Wynne

(57) ABSTRACT

A kit, a needle receiving object and aids, as well as a method of using them, are disclosed for practicing hypodermic needle insertion techniques. At least one aid is disclosed for use with a needle receiving object to facilitate practicing needle insertions. The aid includes at least one template having anatomical landmark indicia and needle insertion site indicia. The needle insertion site indicia is disposed within the confines of the landmark indicia, wherein the needle insertion site indicia serves as a guide for proper needle insertion.

16 Claims, 3 Drawing Sheets

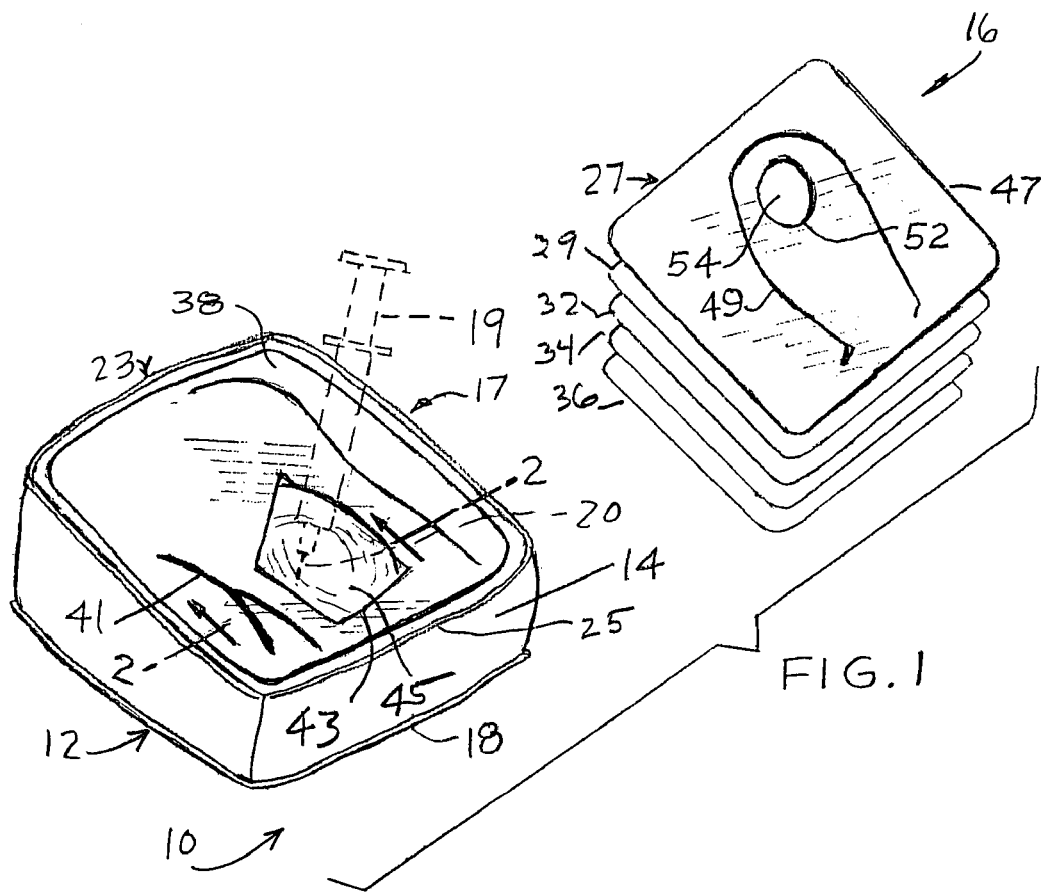
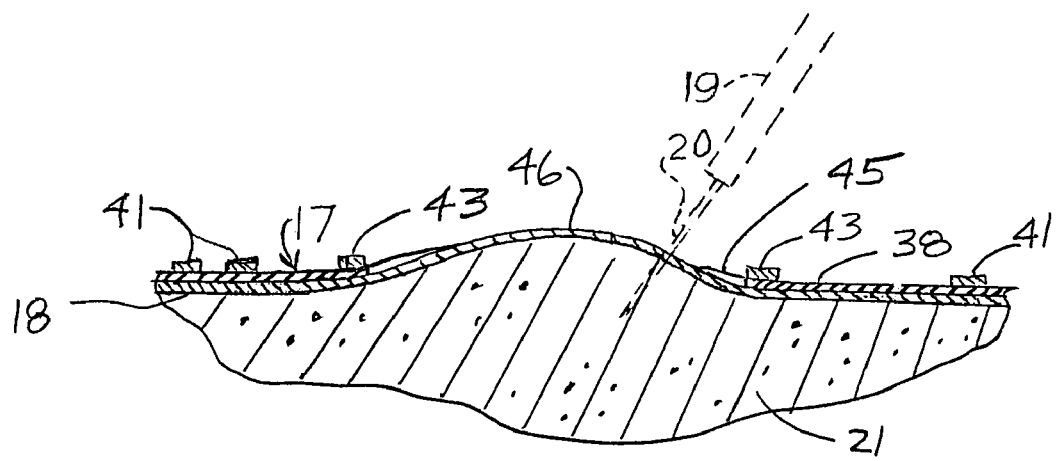

KIT, INJECTABLE OBJECT, AIDS AND A METHOD OF USING THEM FOR PRACTICING HYPODERMIC NEEDLE INSERTION TECHNIQUES

FIELD OF THE INVENTION

The present invention relates in general to articles and methods for practicing hypodermic needle insertion techniques. The invention more particularly relates to a kit, an injectable object, and at least one aid for facilitating the practice of providing hypodermic needle insertions on humans or animals.

BACKGROUND ART

There is no admission that the background art disclosed in this section legally constitutes prior art.

People have practiced the skills necessary for needle insertion for hypodermic syringes to either inject substances into people or animals, or alternatively, for aspirating fluids. Various techniques have been employed, such, for example, as inserting hollow hypodermic needles into oranges or grapefruits to experience the actual needle insertion experience on humans and animals.

A more favorable approach has been employed using an injectable pad, such as the pad marketed under the trademark PRACTI INJECTA-PAD by Wallcur, Inc. of San Diego, Calif. Additionally, students learning needle insertion techniques have practiced these techniques on other people who have volunteered to receive the needle injections or aspirations for educational purposes.

DESCRIPTION OF THE DRAWINGS

The features of this invention and the manner of attaining them will become apparent, and the invention itself will be best understood by reference to the following description of certain embodiments of the invention taken in conjunction with the accompanying drawings, wherein:

FIG. 1 is a pictorial view of a kit for practicing needle insertion techniques, the kit being constructed in accordance with an embodiment of the invention;

FIG. 2 is an enlarged sectional view of the aid and the needle receiving object of FIG. 1 taken substantially on line 2-2 thereof;

DETAILED DESCRIPTION OF CERTAIN EMBODIMENTS OF THE INVENTION

Figure 3:
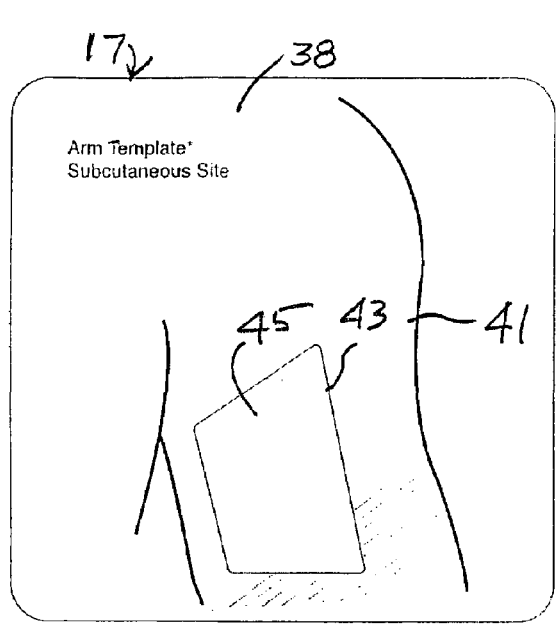
FIGS. 3 through 8 are enlarged face views of the group of aids of FIG. 1.

Certain embodiments of the present invention will now be described more fully hereinafter with reference to the accompanying drawings, in which some, but not all, embodiments of the invention are shown. Indeed, these embodiments of the invention may be in many different forms and thus the invention should not be construed as limited to the embodiments set forth herein; rather, these embodiments are provided as illustrative examples only so that this disclosure will satisfy applicable legal requirements. Like numbers refer to like elements throughout.

It will be readily understood that the components of the embodiments as generally described and illustrated in the drawings herein, could be arranged and designed in a wide variety of different configurations. Thus, the following more detailed description of the embodiments of the system, components and method of the present invention, as represented in the drawings, is not intended to limit the scope of the invention, as claimed, but is merely representative of the embodiment of the invention.

An aid is disclosed for use with a needle receiving object to facilitate practicing needle insertion techniques. The aid includes a template having anatomical landmark indicia and needle insertion site indicia. The needle insertion site indicia is disposed within the confines of the landmark indicia, wherein the needle insertion site indicia serves as a guide for needle insertion.

According to another embodiment of the invention, there is disclosed a needle receiving object for practicing needle insertion techniques. The needle receiving object includes a deformable pad capable of receiving a needle insertion. The needle receiving object includes at least one aid disposed on at least a portion of the object to help visualize an anatomical landmark. The aid is either fixed in place on the injectable object or is removable therefrom. It may be in the form of a template having anatomical landmark indicia and needle insertion site indicia. The needle insertion site indicia are disposed within the confines of the landmark indicia.

According to yet another embodiment of the invention, there is provided an aid for use with a needle receiving object to facilitate practicing needle insertion techniques. The aid may include a template having anatomical landmark indicia and needle insertion site indicia. The needle insertion site indicia are disposed within the confines of the landmark indicia.

Yet another embodiment of the invention relates to a method of practicing needle insertion techniques. The method includes using an injection receiving object, and at least one aid, the aid being in the form of a template having anatomical landmark indicia and needle insertion site indicia. The needle insertion site indicia are disposed within the confines of the landmark indicia. The method includes inserting a needle into the object within the confines of the needle injection site.

A further embodiment of the invention relates to a kit for practicing needle insertion techniques. The kit includes a needle receiving object, and at least one aid for being disposed on at least a portion of the object to help visualize an anatomical landmark. The aid may be in the form of a template having anatomical landmark indicia and needle insertion site indicia. The needle insertion site indicia being disposed within the confines of the landmark indicia. The needle insertion site indicia serves as a guide for proper needle insertion purposes.

Referring now to the drawings, and more particularly to FIGS. 1 and 2 thereof, there is shown a kit 10 for practicing needle insertion techniques in accordance with an embodiment of the present invention. The kit 10 includes a needle receiving object 12 in the form of a deformable pad 14, and a group of aids 16, such as an aid 17, to be disposed on at least a portion of the object 12 for helping visualize an anatomical landmark to facilitate needle insertion into the desired portion of the human or animal body.

The injection receiving object 12 includes a pierceable housing 18, which may be composed of suitable pliable imperforate material such as vinyl material for confining a needle receiving substance 21 such as a suitable gel. A hypodermic syringe having a hypodermic needle 20 is able to pierce the housing 18 and extend into the needle receiving substance 21 for practicing needle insertion techniques. The needle receiving object 12 may be purchased from Wallcur Inc., of San Diego, Calif. under the trademark "PRACTI INJECTA-PAD."

The needle receiving object 12 includes an aid retainer 23 on the upper boundary of the housing 18 in the form of a raised border 25 to help limit the lateral movement of the aid resting on the top surface of the housing 18.

Considering now the aids in greater detail, the kit 10 includes six aids comprising aids 17, 27, 29, 32, 34 and 36. It should be understood that there may be any number of aids employed in the kit 10. Each aid represents a different anatomical landmark site for a needle insertion visualization.

As shown in the drawings, each aid is generally square in shape, but other rectangular shapes or others may be employed. However, other shapes such as generally circular or oval shapes may also be employed. Each aid is in the form of a pliable sheet of material, and may be composed of paper, woven or non-woven fabric, film, or other.

The aid 17 will now be described in greater detail with reference to FIGS. 1 and 2 of the drawings. The aid 17 is in the form of a template 38 having an anatomical landmark indicia 41 on the top face thereof configured in the shape of the back portion of a human right shoulder and right upper arm portion. The template 38 further includes a needle insertion site indicia 43 disposed within the confines of the anatomical landmark indicia 41. The needle insertion site indicia serves as a guide for locating the desired needle insertion portion of the anatomical landmark site. The needle insertion site indicia 43 defines an opening 45 to permit the needle 20 to engage the housing 18 of the object 12. In so doing, a person (not shown) can squeeze or manipulate with the fingers the template 38 and the underlying wall of the housing 18 to pucker or bulge the housing 18 within the needle insertion site indicia opening 45 to simulate the actual manipulation of the tissue and muscle of a human or other animal during the needle insertion procedure. In this regard, as shown in FIG. 2, a portion 46 of the housing 18 is forced by the fingers (not shown) to bulge upwardly to extend through the opening 45 for receiving the needle 20.

Figure 4:
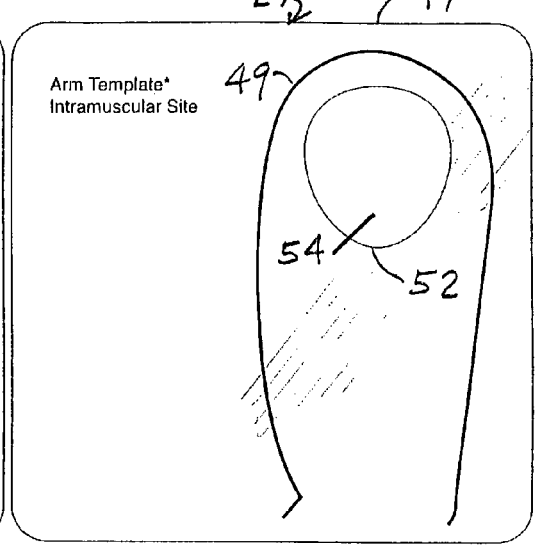

Referring now to FIG. 4, the aid 27 includes a template 47 having an anatomical landmark indicia 49 configured in the shape of an upper side portion of a left arm. A needle insertion site indicia 52 is disposed within the landmark indicia 49 to define an opening 54 for simulating intramuscular needle insertions.

Figure 5:
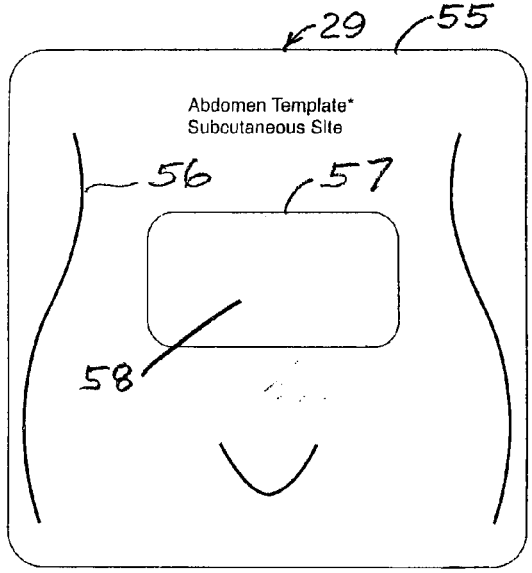

As shown in FIG. 5, the aid 29 includes a template 55 having an anatomical landmark indicia 56 configured in the shape of an abdomen. A needle insertion site indicia 57 defines an opening 58 for subcutaneous injections.

Figure 6:
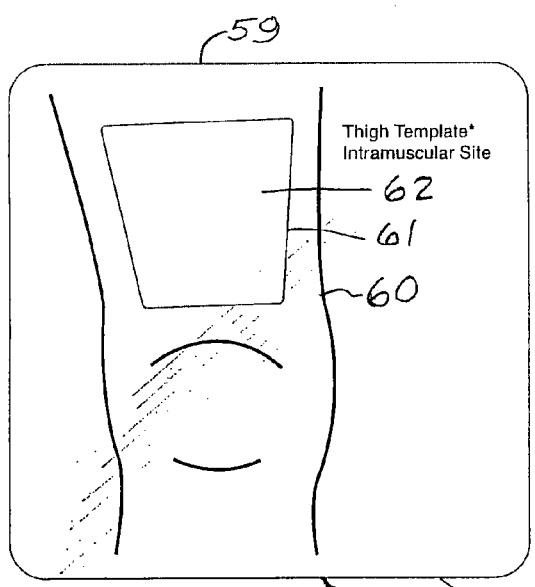

Referring now to FIG. 6, there is shown the aid 32, which includes a template 59 having an anatomical landmark indicia 60 configured in the shape of the upper front of a human thigh and knee, and confining a needle insertion site indicia 61 for visualizing the intra-muscular site for a front portion of a thigh of a human person.

Figure 7:
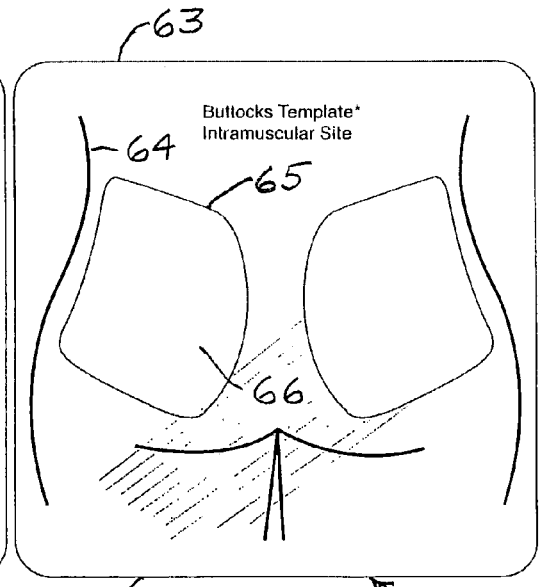

As shown in FIG. 7, the aid 34 includes a template 63 having an anatomical landmark indicia 64 configured in the shape of buttocks. The template 63 includes a pair of anatomical landmark indicia such as the indicia 65 defining an opening 66. In practice, the user is taught to visualize that each one of the needle insertion site indicia should be divided into four quadrants and the outer-upper quadrant is the site for the needle insertion.

Figure 8:
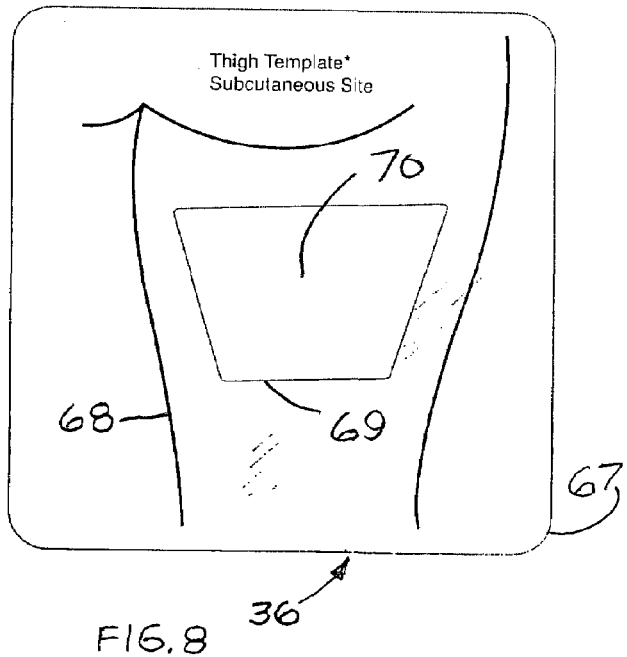

The aid 36 shown in FIG. 8 includes a template 67 having an anatomical landmark indicia 68 configured in the shape of the rear of a thigh of a human person. The template 36 includes a needle insertion site indicia 69 for guiding a needle insertion through an opening 70.

Figure 9:
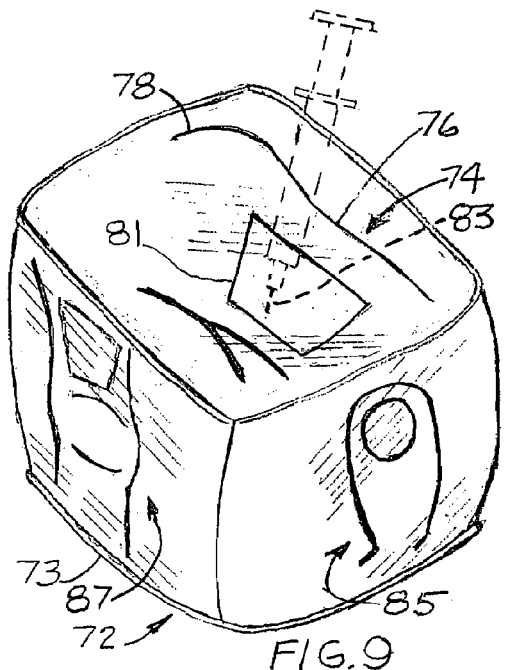
FIG. 9 is a needle receiving object for practicing needle insertion techniques, which is constructed in accordance with another embodiment of the invention.

Referring now to FIG. 9, there is shown another needle receiving object 72 which is constructed in accordance with another embodiment of the invention. The needle receiving object 72 is generally similar to the object 12, except that the object 72 is generally cube shaped and has aids fixed to several faces, such as all six faces, of the cube shaped object.

The needle receiving object 72 includes a cube shaped housing 73 having an aid 74 disposed on a face of the object to help visualize an anatomical landmark. The aid 74 is in the form of a fixed template 76 having landmark indicia 78 configured in the shape of the back of a right arm similar to the indicia 41 of FIG. 1. The template 76 further includes a needle insertion site indicia 81 disposed within the anatomical landmark indicia 78 for helping to visualize the proper needle insertion area for receiving a hypodermic needle 83. In the embodiment shown in FIG. 9, the indicia 78 and 81 may be in the form of a coating such as ink which is deposited on or otherwise fixed to an upper face of the housing for the injectable object 72. Unlike the needle insertion site indicia 43 of FIGS. 1, 2 and 3, the needle insertion site indicia 81 does not define an opening.

The other faces of the cube shaped housing may also include different templates such as templates 85 and 87. Thus, different faces of the object 72 may be positioned on top and used to practice needle insertion utilizing the template disposed on top.

It should be understood that the devices and methods described and shown herein may be utilized by students learning needle insertion techniques for use on other humans or animals, or by persons learning to give injections to themselves.

Although the invention has been described with reference to the above examples, it will be understood that many modifications and variations are contemplated within the true spirit and scope of the embodiments of the invention as disclosed herein. Many modifications and other embodiments of the invention set forth herein will come to mind to one skilled in the art to which the invention pertains having the benefit of the teachings presented in the foregoing descriptions and the associated drawings. Therefore, it is to be understood that the invention shall not be limited to the specific embodiments disclosed and that modifications and other embodiments are intended and contemplated to be included within the scope of the appended claims. Although specific terms are employed herein, they are used in a generic and descriptive sense only and not for purposes of limitation.

What is claimed is:

1. A kit for practicing needle insertion techniques, comprising:

needle receiving object being in the form of a deformable pad having a substantially box shape and a pierceable housing confining a needle receiving substance and adapted to simulate a plurality of body locations;

the housing being composed of pliable imperforate material adapted to be puckered manually;

a plurality of aids, each aid adapted for being disposed on at least a portion of the object to help visualize an anatomical landmark;

each aid being a flat, pliable template each having different anatomical landmark indicia and needle insertion site indicia, the needle insertion site indicia being disposed within the confines of the landmark indicia;

the anatomical landmark indicia being configured in the shape of a portion of a human body;

the needle insertion site indicia at least partially defining an opening for permitting access to the object and serves as a guide for needle insertion;

the pad including means for limiting the lateral movement of the aid resting on the top surface of the housing; and wherein the template and the underlying housing can be squeezed manually to pucker the housing within the needle insertion site indicia opening to simulate the actual manipulation of human tissue and muscle during needle insertion.

2. A kit of claim 1, wherein the anatomical landmark indicia is configured in the shape of the back portion of an arm.

3. A kit of claim 1, wherein the anatomical landmark indicia is configured in the shape of the upper side portion of an arm.

4. A kit of claim 1, where in the anatomical landmark indicia is configured in the shape of an abdomen.

5. A kit of claim 1, wherein the anatomical landmark indicia is configured in the shape of the upper front portion of a thigh.

6. A kit of claim 1, wherein the anatomical landmark site indicia is configured in the shape of buttocks.

7. A kit of claim 1, wherein the anatomical landmark site indicia is configured in the shape of the rear portion of a thigh.

8. A kit of claim 1, wherein the template is composed of a material selected from a group consisting of paper, non-woven fabric, film and woven fabric.

9. A kit of claim 1, wherein the aid is generally rectangular in shape.

10. A needle receiving object for practicing needle insertion techniques, comprising:

a deformable pad capable of receiving needle insertions and having a substantially box shape and a pierceable housing confining a needle receiving substance and adapted to simulate a plurality of body locations;

the housing being composed of pliable imperforate material adapted to be puckered manually;

an aid disposed on at least a portion of the pad to help visualize an anatomical landmark;

the aid being a flat, pliable template having anatomical landmark indicia and needle insertion site indicia, the needle insertion site indicia being disposed within the confines of the landmark indicia;

the anatomical landmark indicia being configured in the shape of a portion of a human body;

the needle insertion site indicia at least partially defining an opening for permitting access to the object and serves as a guide for needle insertions;

the pad including means for limiting the lateral movement of the aid resting on the top surface of the housing; and wherein the template and the underlying housing can be squeezed manually to pucker the housing within the needle insertion site indicia opening to simulate the actual manipulation of human tissue and muscle during needle insertion.

11. A needle receiving object of claim 10, wherein the aid is fixed to the pad.

12. A needle receiving object of claim 10, wherein the aid is removable from the pad.

13. A needle receiving object of claim 10, wherein the pad is generally in the shape of a cube, two or more of the faces having a different aid affixed thereto.

14. A method of practicing a needle insertion technique, comprising:

using a needle receiving object having a pierceable pliable housing confining a needle receiving substance and adapted to simulate a plurality of body locations;

using at least one aid in the form of a template having anatomical landmark indicia and needle insertion site indicia, the needle insertion site indicia at least partially defining an opening for permitting access to the object and being disposed within the confines of the landmark indicia;

placing the template in overlying relationship on the pliable housing of the object;

squeezing the template and the underlying housing to pucker the housing within the needle insertion site indicia opening to simulate the actual manipulation of human tissue and muscle during needle insertion; and inserting a needle into the object within the confines of the needle insertion site indicia.

15. A method of claim 14, further including removing the aid, and replacing it with another aid at least partially disposed on the needle receiving object.

16. A method of claim 14, wherein the needle receiving object has a plurality of aids affixed to a plurality of faces of the object, and further including repositioning the object to permit access to a different aid for practicing needle insertion techniques thereon.

\* \* \* \* \*